United States Patent
Frutuoso et al.

(10) Patent No.: US 10,054,552 B1
(45) Date of Patent: Aug. 21, 2018

(54) SYSTEM AND METHOD FOR AUTOMATED FLUORESCENT PENETRANT INSPECTION

(71) Applicant: United Technologies Corporation, Farmington, CT (US)

(72) Inventors: Sergio S. Frutuoso, Avon, CT (US); Alan Matthew Finn, Hebron, CT (US); Gene B. Donskoy, Farmington, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 0 days.

(21) Appl. No.: 15/716,911

(22) Filed: Sep. 27, 2017

(51) Int. Cl.
G01N 21/91 (2006.01)
G01N 35/00 (2006.01)
G01N 21/88 (2006.01)

(52) U.S. Cl.
CPC ......... *G01N 21/91* (2013.01); *G01N 21/8806* (2013.01); *G01N 21/8851* (2013.01); *G01N 35/00584* (2013.01); *G01N 2021/8887* (2013.01)

(58) Field of Classification Search
USPC ........................................................ 250/302
See application file for complete search history.

(56) References Cited

U.S. PATENT DOCUMENTS

| 6,701,615 | B2 | 3/2004 | Harding et al. |
| 7,215,807 | B2 | 5/2007 | Nomoto et al. |
| 8,744,166 | B2 | 6/2014 | Scheid et al. |
| 8,761,490 | B2 | 6/2014 | Scheid et al. |
| 8,781,209 | B2 | 7/2014 | Scheid et al. |
| 8,781,210 | B2 | 7/2014 | Scheid et al. |
| 8,792,705 | B2 | 7/2014 | Scheid et al. |

(Continued)

FOREIGN PATENT DOCUMENTS

| WO | 9702484 A1 | 1/1997 |
| WO | 2014184337 A1 | 11/2014 |

OTHER PUBLICATIONS

U.S. Appl. No. 15/201,176. "Systems and Methods for Detecting Damage." filed Jul. 1, 2016. Downloaded from Anaqua.

(Continued)

*Primary Examiner* — Kiet T Nguyen
(74) *Attorney, Agent, or Firm* — Carlson, Gaskey & Olds, P.C.

(57) ABSTRACT

An example method of inspecting a part includes applying a penetrant dye to the part, the penetrant dye exhibiting a fluorescent color when subjected to light from a lighting device. A portion of the part is illuminated with light from the lighting device. An image of the portion of the part is automatically recorded with a camera while the portion is illuminated. An uncertainty metric for the image is automatically determined that is indicative of a likelihood that pixels in the image having the fluorescent color represent damage to the part. At least one of the part, lighting device, and camera are automatically adjusted based on the uncertainty metric being within a predefined range. The automatic recording, determining, and adjusting steps are iteratively repeated until the uncertainty metric is greater than the predefined range, or a predefined number of iterations have been performed for the portion of the part.

20 Claims, 3 Drawing Sheets

(56) References Cited

U.S. PATENT DOCUMENTS

| | | |
|---|---|---|
| 9,020,878 B2 | 4/2015 | Kush et al. |
| 2002/0098588 A1* | 7/2002 | Sammak .............. G01N 21/278 436/172 |
| 2005/0270639 A1* | 12/2005 | Miki .................. G02B 21/0088 359/381 |
| 2008/0019921 A1* | 1/2008 | Zhang ................ A61K 49/0004 424/9.6 |
| 2013/0113915 A1 | 5/2013 | Scheid et al. |
| 2015/0192526 A1 | 7/2015 | Nissen et al. |

OTHER PUBLICATIONS

U.S. Appl. No. 15/222,548. "Systems and Methods for Indexing and Detecting Components." filed Jul. 28, 2016. Downloaded from Anaqua.

\* cited by examiner

SYSTEM AND METHOD FOR AUTOMATED FLUORESCENT PENETRANT INSPECTION

BACKGROUND

The present disclosure relates to part inspection, and more particularly to a system and method for automated fluorescent penetrant inspection.

Gas turbine engine components can suffer wear and in some cases damage from operation. Fluorescent penetrant inspection (FPI) is a known technique for non-destructive inspection of parts, such as turbine blades of a gas turbine engine, for cracks. In FPI, a fluorescent dye is applied to a component and, after various standard dye processing steps, the part is manually inspected using ultraviolet (UV) light that causes the dye to fluoresce. Manual visual inspection of FPI images is both time consuming and error prone, due in part to inconsistency between human inspectors.

SUMMARY

One example embodiment of a method of inspecting a part includes applying a penetrant dye to the part, the penetrant dye exhibiting a fluorescent color when subjected to light from a lighting device. A portion of the part is illuminated with light from the lighting device. An image of the portion of the part is automatically recorded with a camera while the portion is illuminated. An uncertainty metric for the image is automatically determined that is indicative of a likelihood that pixels in the image having the fluorescent color represent damage to the part. At least one of the part, lighting device, and camera are automatically adjusted based on the uncertainty metric being within a predefined range. The automatic recording, determining, and adjusting steps are iteratively repeated until the uncertainty metric is greater than the predefined range, or a predefined number of iterations have been performed for the portion of the part.

In another example embodiment of the above described method, the light is ultraviolet (UV) light.

In another example embodiment of any of the above described methods, automatically adjusting at least one of the part, the lighting device, and the camera includes automatically adjusting at least one of the following: a relative position of the part with respect to one or both of the lighting device and the camera; and an orientation of one or more of the part, the lighting device, and the camera.

In another example embodiment of any of the above described methods, automatically adjusting at least one of the part, the lighting device, and the camera based includes at least one of: automatically adjusting one or more of a light intensity, light illumination area, and polarization of the lighting device; and automatically adjusting an exposure setting of the camera to accommodate the adjustment to the lighting device.

In another example embodiment of any of the above described methods, the method includes determining that the portion of the part is damaged based on the uncertainty metric being greater than the predefined range; and determining that the portion of the part is not damaged based on the uncertainty metric not exceeding the predefined range for any of the iterations.

In another example embodiment of any of the above described methods, the method includes, based on a determination that the portion of the part is damaged, automatically depositing a damage marker on the part in proximity to the damage.

In another example embodiment of any of the above described methods, determining an uncertainty metric for the image includes: converting the image, which uses a first color representation, to a second image that uses a different, second color representation; performing a color detection to determine areas in the second image having the fluorescent color; performing a pattern detection based on the color detection; and determining a likelihood that a detected pattern depicts damage to the part based on pattern matching with a defect model.

In another example embodiment of any of the above described methods, the method includes situating a fiducial marker that exhibits the fluorescent color in close enough proximity to the portion of the part that it is recorded as part of the image; wherein said performing a color detection is performed based on the fiducial marker in the image.

In another example embodiment of any of the above described methods, performing a pattern detection includes: creating a skeleton image based on the color detection; and performing a Hough transform of the skeletal image.

In another example embodiment of any of the above described methods, the method includes situating a light filter between the part and a portion of either the camera or the lighting device when recording images, the light filter preventing one or more of certain non-UV light and light polarizations from passing through the filter.

In another example embodiment of any of the above described methods, the method includes situating the camera, which is part of a borescope, inside the part when recording images of the portion of the part.

One example embodiment of a part inspection system includes a part onto which a penetrant dye is applied, the penetrant dye exhibiting a fluorescent color when subjected to light within a given frequency band; a lighting device operable to project light within the given frequency band onto the part; a camera; and a controller. The controller is configured to: automatically record an image of a portion of the part with the camera while the portion is illuminated by the light within the given frequency band; automatically determine an uncertainty metric for the image indicative of a likelihood that pixels in the image having the fluorescent color represent damage to the part; and automatically adjust at least one of the part, the lighting device, and the camera based on the uncertainty metric being within a predefined range. The controller is configured to iteratively repeat the automatic recording, determining, and adjusting until the uncertainty metric is greater than the predefined range, or a predefined number of iterations have been performed for the portion of the part.

In another example embodiment of the above described part inspection system, the system includes at least one robotic arm operable to move with six degrees of freedom, wherein said automatically adjusting at least one of the part, the light, and the camera based includes manipulating the at least one robotic arm to adjust at least one of the following: a relative position of the part with respect to one or both of the lighting device and the camera; and an orientation of one or more of the part, the lighting device, and the camera.

In another example embodiment of any of the above described part inspection systems, to automatically adjust at least one of the part, the lighting device, and the camera, the controller is configured to perform at least one of: automatically adjusting one or more of a light intensity, light illumination area, and polarization of the lighting device; and automatically adjusting an exposure setting of the camera to accommodate the adjustment to the lighting device.

In another example embodiment of any of the above described part inspection systems, the controller is configured to: determine that the portion of the part is damaged based on the uncertainty metric being greater than the predefined range; and determine that the portion of the part is not damaged based on the uncertainty metric not exceeding the predefined range for any of the iterations.

In another example embodiment of any of the above described part inspection systems, the system includes a marking device, and the controller is configured to automatically deposit a damage marker on the part in proximity to the damage based on a determination that the portion of the part is damaged.

In another example embodiment of any of the above described part inspection systems, to determine an uncertainty metric for the image, the controller is configured to: convert the image, which uses a first color representation, to a second image that uses a different, second color representation; perform a color detection to determine areas in the second image having the fluorescent color; perform a pattern detection based on the color detection; and determine a likelihood that a detected pattern depicts damage to the part based on pattern matching with a defect model.

In another example embodiment of any of the above described part inspection systems, to perform a pattern detection, the controller is configured to: create a skeleton image based on the color detection; and perform a Hough transform of the skeletal image.

In another example embodiment of any of the above described part inspection systems, the given frequency band includes ultraviolet light, and the part inspection system includes a light filter situated between the part and a portion of either the camera or the lighting device when the camera records an image of the part, the light filter operable to prevent one or more of certain non-UV light and light polarizations from passing through the filter.

In another example embodiment of any of the above described part inspection systems, the camera is part of a borescope, and is situated within the part when recording images of the part.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

Figure 1:
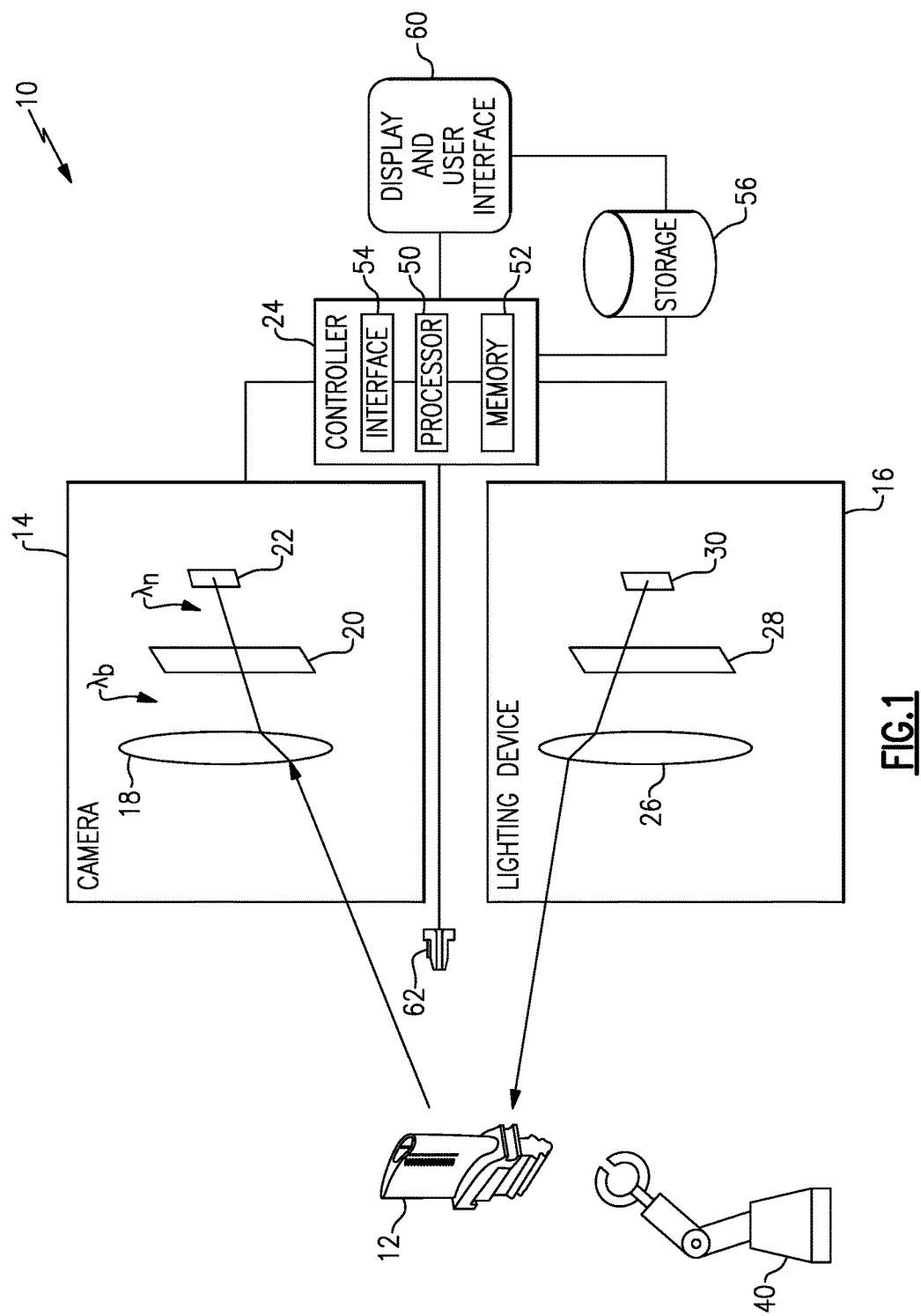
FIG. 1 is a schematic view of an example part inspection system.

FIG. 1 is a schematic view of an example FPI part inspection system 10 that includes a part 12, a camera 14, and a lighting device 16. In the example of FIG. 1, the part 12 is a turbine blade of a gas turbine engine. A penetrant dye is applied to the part 12 that exhibits a fluorescent color (e.g., green, blue, or a blue-green) when subjected to light having a wavelength corresponding to an excitation frequency of the penetrant dye.

In some examples, including the discussion below, the light corresponding to the excitation frequency is a UV light. In other examples, the light is non-UV light (e.g., above or below UV light in the electromagnetic spectrum) or the penetrant dye exhibits fluorescence at a frequency or band of frequencies that is non-visible (e.g., above or below visible light in the electromagnetic spectrum). Thus, the techniques discussed herein are not limited to using dyes that require UV light to fluoresce in the visible spectrum.

The camera 14 is operable to record images of the part 12 while the part 12 is illuminated by UV light from lighting device 16. The camera 14 includes a lens 18 and an imaging sensor 22, and optionally includes a filter 20. The imaging sensor 22 is a focal-plane array (FPA) sensor in one example. Various settings of the camera 14 are automatically controllable by a controller 24 (e.g., f-stop/aperture, shutter speed, ISO light sensitivity, zoom, focus, and so on). If included, the optional filter 28 can be a polarizing filter or a bandpass filter, for example. In an alternative configuration to that depicted in FIG. 1, the optional filter 20 is situated between the lens 18 and the part 12.

In some examples, the camera 14 is sensitive to radiation in the visible region of the electromagnetic spectrum. In the same or other examples, the camera 14 is sensitive to radiation above or below the visible region of the electromagnetic spectrum.

The lighting device 16 includes a lens 26 and a UV light source 30 and optionally includes a filter 28. The UV light source 30 projects UV light through the optional filter 28 (if included) and through the lens 26 onto the part 12. The emitted UV light is provided at least at an excitation frequency of the penetrant dye. Settings of the lighting device 16 are automatically controllable as well (e.g., intensity, polarization, zoom, focus, and so on). In one example, controlling the zoom of the lighting device 16 includes automatically adjusting a distance between the lens 26 and the UV light source 30, internal lenses of lens 26, or the part 12, for example, to narrow/brighten or dim/widen the UV light projected onto the part 12. If included, the optional filter 28 can be a polarizing filter or a bandpass filter, for example. In an alternative configuration to the one depicted in FIG. 1, the optional filter 28 is situated between the lens 26 and the part 12. In one example, the lighting device 16 is attached to the camera 14

In the example of a polarizing filter 20 and/or 28, the filter controls the polarization of light that passes through the filter (e.g., to exclude certain light polarizations). In the example of a bandpass filter 20 and/or 28, the filter controls one or more of a wavelength of light and a band of wavelengths of light that pass through the filter. In the particular example depicted in FIG. 1, the light that passes through lens 18 has a first range of wavelengths represented as $\lambda_b$, and the optional filter 20 acts as a bandpass filter that permits a narrower range of wavelengths, represented as $\lambda_n$, to pass to the imaging sensor 22.

The filters 20 and/or 28 may be designed as bandpass filters that to pass more than one frequency of light, which includes an excitation frequency of the penetrant dye, such that a structure of the part 12 remains visible, but the fluorescent color dominates the imagery. In one example, the wavelength range $\lambda_n$ includes primarily or exclusively UV light.

The controller 24 is operable to automatically control the settings and operation of at least one of the camera 14 and lighting device 16 to record images of the part 12 while the part is illuminated by UV light from the lighting device 16.

Some camera features, such as autofocus, may be built into the camera 14 or may be implemented by the controller 24 (e.g., using a known technique such as a sweep of a parameter range with optimization by selecting the maximum, where the focus is varied through the range and the best focus is chosen to maximize the high frequency components of a spatial Fourier transform).

In one embodiment, the controller 24 automatically records an image of a portion of the part 12 with the camera 14 while the portion is illuminated by UV light from lighting device 16. If the recorded image has fluorescent portions, those portions may represent actual damage, or they may represent non-damaged areas. For example, if the part 12 has been brazed to deposit material onto the part, some of the penetrant dye may cause a porous portion of those brazed areas to appear as fluorescent. The controller 24 analyzes the recorded image and automatically determines an uncertainty metric for the image indicative of a likelihood that pixels in the image having the fluorescent color represent damage to the part 12. If the uncertainty metric is greater than a predefined range of values, then the controller 24 determines that the part 12 is damaged.

In one embodiment, the controller 24 automatically records a first image of a portion of the part 12 with the camera 14 while the portion is illuminated by UV light from lighting device 16 and a second image of a portion of the part 12 with the camera 14 while the portion is not illuminated by UV light from lighting device 16. If there is a difference between the first and second images, this difference represents the fluorescent portions, those portions may represent actual damage, or they represent non-damaged areas as described previously. The controller 24 may record the second image of a portion of the part 12 with the camera 14 while the portion is not illuminated by UV light from lighting device 16 by turning off lighting device 16, or by controlling one or more of filters 20, 28 to selectively pass or not pass UV light.

The controller 24 compares the uncertainty metric to a predefined range having an upper bound and a lower bound. If the uncertainty metric is greater than the upper bound, then the controller 24 determines that the part 12 is damaged. If the controller 24 determines that the uncertainty metric is below the lower bound during a first iteration or first plurality of iterations, it determines that the part 12 is not damaged. If the uncertainty metric is between the upper and lower bounds (i.e., in the predefined range), then additional images are recorded to try and resolve the uncertainty.

In particular, if the uncertainty metric is within the predefined range of values, the controller 24 automatically adjusts at least one of the part 12, the lighting device 16, and the camera 14, and iteratively repeats the automatic recording, automatic determining, and automatic adjusting until the uncertainty metric is greater than the predefined range (indicating damage), or a predefined number of iterations have been performed for the portion of the part. In some examples, the controller 24 determines that the portion of the part 12 is not damaged based on the uncertainty metric not exceeding the predefined range for any of the iterations.

The system 10 includes at least one robotic device 40 that controls positional and orientation adjustments of at least one of the part 12, camera 14, and lighting device 16 for capturing images of different views of the part 12. In some examples, each of the part 12, camera 14, and lighting device 16 are controlled by a respective robotic device 40. In other examples, the position and/or orientation of one or more of the part 12, camera 14, and lighting device 16 are manually manipulated by a technician.

In the example of FIG. 1, the at least one robotic device 40 is a robotic arm that has six degrees freedom (i.e., X, Y, Z axis movement, plus pitch, yaw, roll rotation). In one example, the at least one robotic device 40 includes a revolving platform onto which the part 12 is mounted.

The controller 24 includes a processor 50, memory 52, and interface 54. The processor 50 may include one or more microprocessors, microcontrollers, application specific integrated circuits (ASICs), or generally any device capable of executing software instructions.

The memory 52 is a computer-readable storage medium and may include any one or combination of volatile memory elements (e.g., random access memory, RAM, such as DRAM, SRAM, SDRAM, VRAM, and so on) and/or non-volatile memory elements (e.g., ROM, hard drive, tape, CD-ROM, and so on), for example. Moreover, the memory 52 may incorporate electronic, magnetic, optical, and/or other types of storage media. The memory 52 can also have a distributed architecture, where various components are situated remotely from one another, but can be accessed by the processor 52. The memory stores program instructions that configure the controller 24 to carry out the techniques discussed herein.

The interface 54 can include, for example but not limited to, one or more ports, buses, and/or wired or wireless connections for receiving input and/or sending information (e.g., to another device, such as an electronic display). The interface 54 may provide wired and/or wireless communication functionality, for example.

A storage device 56 (which may be internal or external to the controller 24) stores a damage model for damage detection.

A combined display/user interface (UI) device 60, which may include a touchscreen, facilitates interaction with the controller 24.

Optionally, the system 10 may include a marking device 62, such as an inkjet printing head, for marking parts that the controller 24 determines are damaged. One example marking could include one or more dots applied to the part 12. In other examples, more detailed information could be provided in a marking. The marking device 62 may mark the part 12 in proximity to a damaged area, for example. The controller 24 controls the marking device 62, which also may be controlled by a robotic device 40, based on automatic consultation with a three-dimensional model of the part (e.g., stored in memory 52 or storage 56). Damage may be additionally or solely marked electronically on a three-dimensional model of the part or otherwise recorded in a memory 52 or storage 56 for subsequent use.

In one example, the marking device 62 marks the part 12 on or in proximity to the damaged area to facilitate repair by a technician. Alternatively, an ink marking can be provided by a human inspector based on feedback provided on the combined display/UI device 60. Some example inks that could be utilized include a high temperature, non-reactive blue ink such as DYKEM® High Temp 44 Medium Blue (Item #44094 from American Marking, Inc.), or the ink described in US Application No. 2003/0101899 to Hartanto. Such inks are suitable for marking the parts 12 in a way that does not degrade their coating or otherwise impede the functionality, reparability, or durability of the part 12.

Figure 2:
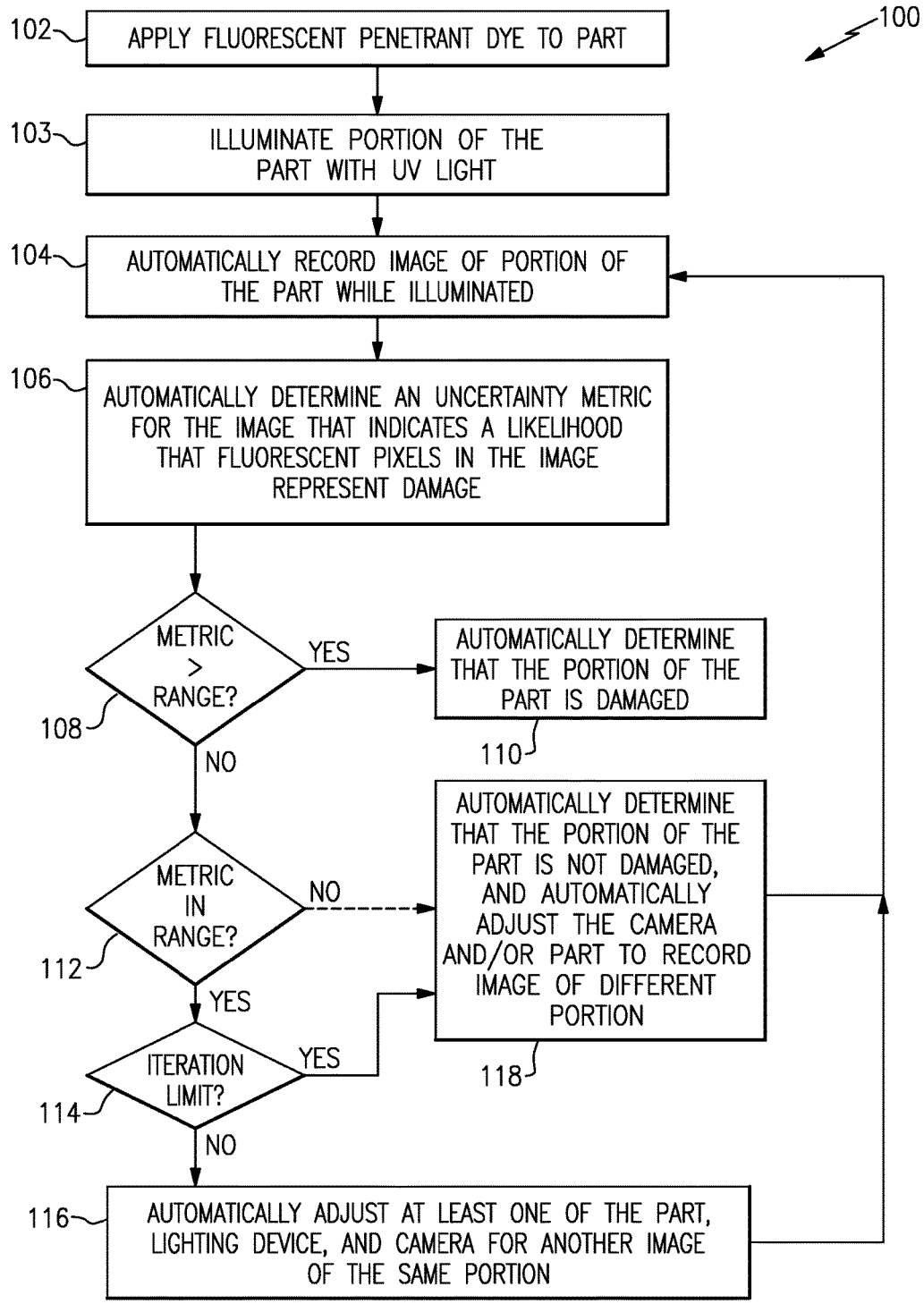
FIG. 2 is flowchart of an example method of inspecting a part.

Referring now to FIG. 2, flowchart of an example method 100 of inspecting a part 12 based on image analytics and feedback control is shown. A penetrant dye that exhibits a fluorescent color when subjected to UV light is applied onto the part 12 (block 102). This may include other standard FPI steps which are known, such as cleaning and drying the part 12 before application of the penetrant dye, and after application: removing excess penetrant, drying the part 12, and applying a developer solution.

A portion of the part 12 is illuminated with UV light from the lighting device 16 (block 103). The controller 24 uses camera 14 to automatically record an image of a portion of the part 12 while the portion is illuminated by the UV light from the lighting device 16 (block 104).

The controller automatically determines an uncertainty metric for the image that indicates a likelihood that pixels in the image having the fluorescent color represent damage to the part 12 (block 106). The controller then compares the uncertainty metric to a predefined range.

If the metric is greater than the range of values (a "yes" to block 108), the controller 24 automatically determines that the portion of the part is damaged (block 110).

If the metric is in the predefined range of values (a "yes" to block 112) and an iteration limit has not yet been reached (a "no" to block 114), the controller 24 automatically adjusts at least one of the part 12, the lighting device 16, and the camera 14 for another image of the same portion (block 116), and returns to block 104 for another iteration.

Otherwise, if the iteration limit has been reached (a "yes" to block 114), the controller 24 automatically determines that the portion is not damaged, and automatically adjusts the camera 14 and/or part 12 to record an image of a different portion of the part 12 (block 118).

In some examples, if the metric is below the predefined range during a first iteration (a "no" to block 112), then the controller 24 proceeds to block 118. However, the controller would not transition from block 112 directly to block 118 during a second iteration, because it is already known that an image of the portion has an uncertainty metric within the range.

The iterations repeat until the uncertainty metric is greater than the predefined range (a "yes" to block 108) or a predefined number of iterations have been performed for the portion of the part (a "yes" to block 114).

The method 100 facilitates a systematic non-destructive inspection of the part 12 based on feedback from FPI images of the part 12, based on both crack detection and the phenomenon of dye fluorescence.

In one example, the automatic adjustment of block 116 comprises adjusting at least one of the part, the light, and the camera based includes automatically adjusting at least one of the following:
 a relative position of the part with respect to one or both of the lighting device 16 and the camera 14; and
 an orientation of one or more of the part 12, the lighting device 16, and the camera 14.

Thus, the controller 24 can move and/or articulate any one of the part 12, camera 14, and lighting device 16 either alone or in combination, and can adjust the relative distances between the part 12, camera 14, and lighting device 16.

In one example, the automatic adjustment of block 116 includes automatically adjusting the UV light output of the lighting device 16 and automatically adjusting an exposure setting of the camera 14 to accommodate the adjusted UV light output. The adjustment to the UV light output could include one or more of a change in light intensity, light illumination area, and polarization of the lighting device 16. Thus, if the lighting device 16 was adjusted to be brighter, an exposure setting of the camera 14 (e.g., shutter speed, f-stop, ISO) could be adjusted accordingly to avoid overexposure.

Adjusting a polarity of the lighting device 16 in some examples includes automatically controlling an electrically controllable polarization filter (e.g., through rotation of a ring of the filter, or through current and/or voltage adjustments applied to molecules in the filter).

Adjusting the lighting device 16 with respect to the part 12 could be useful to better illuminate a potential damage area. For example, a crack may be better illuminated from one side than from an opposite second side. Also, an amount of glow emitted by the remaining penetrant dye can vary due to a number of factors, such as light orientation and light intensity.

Assuming that the controller 24 determines that the part 12 is damaged (block 110), the controller 24 in one example can determine whether the part is repairable or should be discarded based on one or more of a location, a size, a shape, and the like of the damage. If the damage is found in one or more unrepairable locations, for example, the controller 24 can determine that the part should be discarded based on automatic consultation with a three-dimensional model of the part (e.g., stored in memory 52 or storage 56).

In the examples discussed above, the controller 24 is implemented on a computer and utilizes feedback control of uncertainty of detection. In some examples, the controller 24 acts as a non-linear controller that utilizes game theory to determine a light, camera, and part arrangement that will yield additional certainty about whether detected fluorescence indicates damage. Instead of recording images of every possible angle and lighting configuration for the part 12, the controller 24 takes steps to resolve uncertainty in previous images, which is a more efficient approach.

In another example, the controller 24 may sweep a range of one or more light, camera, and part arrangements and select the arrangement that is most informative in resolving any uncertainty of detection. For example, lighting device 16 might be moved from a low oblique angle of 10° with respect to one side the part 12 surface that is currently perpendicular to camera 14 to a similar low oblique angle on the other side of the part 12 surface that is currently perpendicular to camera 14 while taking successive images every 1°. Alternatively, the controller 24 might systematically vary one or more other controllable aspects of system 10 while taking successive images. The controller 24 may determine the uncertainty of detection for each image. The image with the least uncertainty is the most informative in resolving the uncertainty of detection.

Figure 3A:
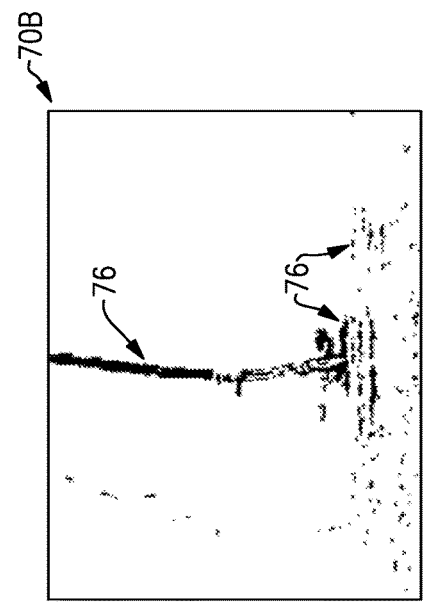
FIG. 3A is an image a portion of a cracked part after application of a fluorescent penetrant dye.

FIG. 3A is an image 70A a portion of an example part 12 that is damaged, after application of a fluorescent penetrant dye. As shown in FIG. 3A, there is a crack 72 on a surface 73 of the part 12 having a portion 74 that extends beneath the surface 73. The image 70A is noticeably fluorescent along the crack 72 including portion 74, but also other areas 75 as well.

Figure 3B:
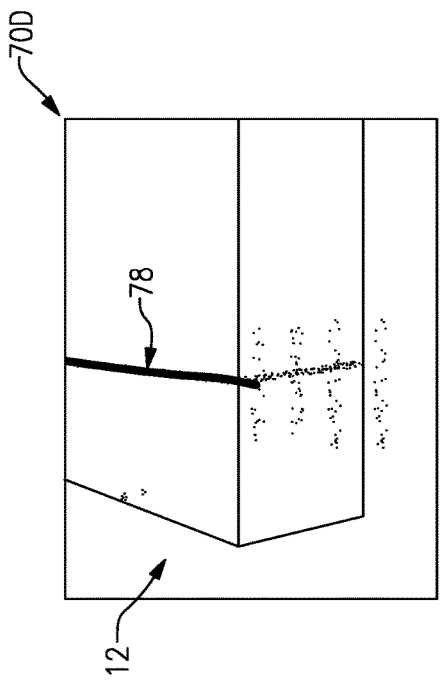
FIG. 3B is a binary image showing areas of excess fluorescent color from the image of FIG. 3A.

FIG. 3B depicts the image 70B of FIG. 3A after conversion into a binary image that only shows excess fluorescent color (shown in black), and white pixels for everything else. In one example, creation of the image 70B involves conversion of the image 70A, which utilizes a red-green-blue (RGB) color representation, to a hue-saturation-brightness (HSV) color representation. Use of the HSV color representation makes detection of excess colors easier to perform.

For example, if the fluorescent color is a fluorescent green, it may be easier to detect excess green in the HSV color representation than in RGB.

Further, it may be more reliable to detect excess color by fusing detections in multiple color representations, e.g., areas where excess color is detected in more than one color space. Yet further, it may be more reliable to detect excess color by fusing detections in multiple registered images areas where excess color is detected in more than one image. This could include fusing multiple images recorded with the camera 14 and part 12 in the same positions in some examples (e.g., multiple image of the same portion of the part at the same or different exposure settings), which could help reduce noise present in the images. In another example, fusing multiple images recorded includes fusing images in which the camera 14 and part 12 are in different positions, and then performing a geometric alignment between those multiple images as part of the fusing.

Alternative methods of fusing detection across different color spaces or images are contemplated, e.g., the fusion may be accomplished by methods including deep neural networks, convolutional neural networks, recursive neural networks, dictionary learning, bag of visual/depth word techniques, Support Vector Machine (SVM), Decision Trees, Decision Forests, Fuzzy Logic, Markov Model techniques, Hidden Markov Models (HMM), Markov Decision Processes (MDP), Partially Observable MDPs, Markov Decision Logic, Probabilistic Programming, Bayesian inference, and the like. Areas of excess fluorescent color in the binary image 70B are shown with reference numeral 76.

In some examples, the threshold of what constitutes an excess fluorescent color is automatically generated using an algorithm such as one of Otsu's method, the valley emphasis method, the FireFly method, the Fireworks method, multi-level methods, optimization-based methods (e.g., particle swarm optimization), and the like.

In some examples, if a passband filter 20 and/or 28 that restricts color to that of the fluorescent color of the penetrant dye, the color representation conversion and binary image creation steps can be omitted.

In some examples, the controller 24 is configured to situate a fiducial marker (not shown) that exhibits the fluorescent color in close enough proximity to the portion of the part that it is recorded as part of the image. This can be used a baseline for setting an excess color threshold as a built-in self-test (BIST). In such examples, the fluorescent color detection is performed based on the fiducial marker in the image.

Figure 3C:
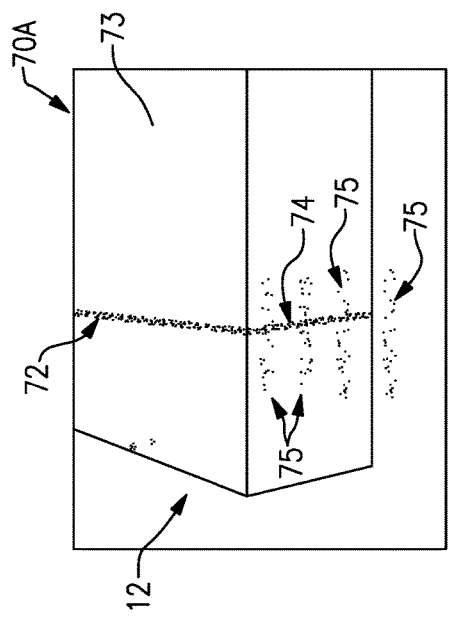
FIG. 3C depicts a skeletal image created based on the image of FIG. 3B.

Having detected areas of excess fluorescent color 76, the controller 24 converts image 70B into the skeletal image 70C of FIG. 3C. Skeletal image conversion algorithms are known in the art, and are not discussed in detail herein. The skeletal image 70C narrows the excess color areas 76 into a narrower, skeletal formation that is suitable for pattern matching against known damage patterns.

Figure 3D:
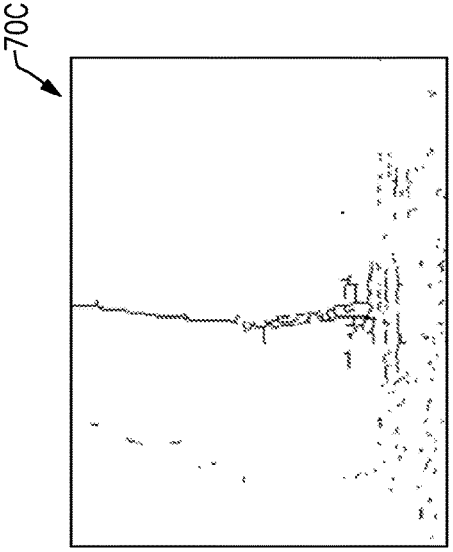
FIG. 3D depicts a detected line superimposed on the image of FIG. 3A.

The controller 24 performs a pattern detection method, such as a Hough transform, to determine a pattern (e.g., one or more lines) in the skeletal image 70C. Image 70D of FIG. 3D depicts a detected pattern in the form of line 78, which is superimposed on top of the image 70A. The controller 24 then determines a likelihood that a detected line 78 depicts damage to the part 12 based on pattern matching with a defect model (e.g., stored in storage 56). Of course, it is understood that other patterns more complex than a line could be detected based on the defect model.

The uncertainty metric represents a probability that a given area corresponds to damage on the part. In some examples, the controller 24 creates a probabilistic map of possible damage areas. For instance, every point on a probabilistic map may be a computed probability that is the minimum of one and the intensity of a fluorescent color divided by the intensity of a fiducial reference color. At every point on the map, the difference of the computed probability from either zero (no probability of damage) or one (certain damage) represents an uncertainty metric.

In some cases a lower and an upper threshold may be denoted to establish a range of probabilities between, but not including, zero and one. When a probability of damage is above the upper threshold, equivalently above the range, controller 24 may determine that damage is present. When a probability of damage is below the lower threshold, equivalently below the range, controller 24 may determine that damage is not present. When a probability of damage is below the upper threshold and at the same time above the lower threshold, equivalently within the range, controller 24 may determine that damage is uncertain and may undertake additional actions, described elsewhere herein, to resolve the uncertainty.

Additional a priori information about "hot spots", crack information, shape information, and the like, in the form of spatial probability density functions (PDFs) may be included in a Bayesian computation of a probabilistic map of possible damage areas. In this example, the probability of damage at every spot may be computed by Bayesian inference wherein the probability is conditional and computed from the prior (unconditional) probability, the prior information (likelihood), and the model evidence (marginal likelihood).

In yet another example, morphological filters may be used directly on images or on a probabilistic map to improve detection, resolve uncertainty, remove noise, and so on. As described elsewhere herein, brazed areas may have a porosity allowing the capture of a fluorescent dye. This captured dye will be visible in images taken by camera 14, but do not necessarily represent damage to part 12. The shape of the fluorescence due to this porosity may be predominantly circular or elliptical and may be morphologically distinct from damage, e.g., cracks which may be piece-wise linear line segments. A morphological filter that detects predominantly circular or elliptical shapes, e.g., Hough Circles or Hough Ellipses, may be applied to an image to detect and remove these shapes. Similarly, the same morphological filter may be applied to a probabilistic map to remove or discount these areas.

Although the camera 14 and lighting device 16 are depicted as being outside of the part 12 in FIG. 1, it is understood that in one example the camera 14 could be part of a borescope that is inserted into a cavity within the part 12. In one such example, the lighting device 16 is part of the borescope and is also inserted into the part. In one example, the lighting device is a fiber optic lighting device that is inserted into the part 12 and emits UV light radially.

Although the lighting device 16 has been discussed above as being a UV lighting device, in some examples the lighting device 16 could emit some or only non-UV light, which could include light in the spectrum that is visible to humans. In one such example, the penetrant dye includes a quantum dot dye that can be illuminated to fluoresce with light in the visible spectrum. Additionally, the camera 14 in some examples is sensitive to radiation above and/or below the visible region of the electromagnetic spectrum.

Although inspection of gas turbine engine parts 12 has been discussed above, it is understood that the system 10 and method 100 could be applied to components of other machines.

Although the steps above have been discussed in a specific order, it is understood that some of the steps could be performed in a different order if desired. For example, the image fusing step discussed above could happen before or after conversion to the HSV color representation.

Also, although example embodiments have been disclosed, a worker of ordinary skill in this art would recognize that certain modifications would come within the scope of this disclosure. For that reason, the following claims should be studied to determine the scope and content of this disclosure.

What is claimed is:

1. A method of inspecting a part, comprising:
applying a penetrant dye to a part, the penetrant dye exhibiting a fluorescent color when subjected to light from a lighting device;
illuminating a portion of the part with light from the lighting device;
automatically recording an image of the portion of the part with a camera while the portion is illuminated;
automatically determining an uncertainty metric for the image indicative of a likelihood that pixels in the image having the fluorescent color represent damage to the part;
automatically adjusting at least one of the part, the lighting device, and the camera based on the uncertainty metric being within a predefined range; and
iteratively repeating the automatic recording, determining, and adjusting steps until the uncertainty metric is greater than the predefined range, or a predefined number of iterations have been performed for the portion of the part.

2. The method of claim 1, wherein the light is ultraviolet (UV) light.

3. The method of claim 1, wherein said automatically adjusting at least one of the part, the lighting device, and the camera comprises automatically adjusting at least one of the following:
a relative position of the part with respect to one or both of the lighting device and the camera; and
an orientation of one or more of the part, the lighting device, and the camera.

4. The method of claim 1, wherein said automatically adjusting at least one of the part, the lighting device, and the camera based comprises at least one of:
automatically adjusting one or more of a light intensity, light illumination area, and polarization of the lighting device; and
automatically adjusting an exposure setting of the camera to accommodate the adjustment to the lighting device.

5. The method of claim 1, comprising:
determining that the portion of the part is damaged based on the uncertainty metric being greater than the predefined range; and
determining that the portion of the part is not damaged based on the uncertainty metric not exceeding the predefined range for any of the iterations.

6. The method of claim 5, comprising:
based on a determination that the portion of the part is damaged, automatically depositing a damage marker on the part in proximity to the damage.

7. The method of claim 1, wherein said determining an uncertainty metric for the image comprises:
converting the image, which uses a first color representation, to a second image that uses a different, second color representation;
performing a color detection to determine areas in the second image having the fluorescent color;
performing a pattern detection based on the color detection; and
determining a likelihood that a detected pattern depicts damage to the part based on pattern matching with a defect model.

8. The method of claim 7, comprising:
situating a fiducial marker that exhibits the fluorescent color in close enough proximity to the portion of the part that it is recorded as part of the image;
wherein said performing a color detection is performed based on the fiducial marker in the image.

9. The method of claim 7, wherein said performing a pattern detection comprises:
creating a skeleton image based on the color detection; and
performing a Hough transform of the skeletal image.

10. The method of claim 1, comprising
situating a light filter between the part and a portion of either the camera or the lighting device when recording images, the light filter preventing one or more of certain non-UV light and light polarizations from passing through the filter.

11. The method of claim 1, comprising
situating the camera, which is part of a borescope, inside the part when recording images of the portion of the part.

12. A part inspection system comprising:
a part onto which a penetrant dye is applied, the penetrant dye exhibiting a fluorescent color when subjected to light within a given frequency band;
a lighting device operable to project light within the given frequency band onto the part;
a camera; and
a controller configured to:
automatically record an image of a portion of the part with the camera while the portion is illuminated by the light within the given frequency band;
automatically determine an uncertainty metric for the image indicative of a likelihood that pixels in the image having the fluorescent color represent damage to the part;
automatically adjust at least one of the part, the lighting device, and the camera based on the uncertainty metric being within a predefined range; and
iteratively repeat the automatic recording, determining, and adjusting until the uncertainty metric is greater than the predefined range, or a predefined number of iterations have been performed for the portion of the part.

13. The part inspection system of claim 12, comprising at least one robotic arm operable to move with six degrees of freedom, wherein said automatically adjusting at least one of the part, the light, and the camera based comprises manipulating the at least one robotic arm to adjust at least one of the following:
a relative position of the part with respect to one or both of the lighting device and the camera; and
an orientation of one or more of the part, the lighting device, and the camera.

14. The part inspection system of claim 12, wherein to automatically adjust at least one of the part, the lighting device, and the camera, the controller is configured to perform at least one of:

automatically adjust one or more of a light intensity, light illumination area, and polarization of the lighting device; and automatically adjust an exposure setting of the camera to accommodate the adjustment to the lighting device.

15. The part inspection system of claim 12, wherein the controller is configured to:

determine that the portion of the part is damaged based on the uncertainty metric being greater than the predefined range; and determine that the portion of the part is not damaged based on the uncertainty metric not exceeding the predefined range for any of the iterations.

16. The part inspection system of claim 15, comprising a marking device, wherein the controller is configured to automatically deposit a damage marker on the part in proximity to the damage based on a determination that the portion of the part is damaged.

17. The part inspection system of claim 12, wherein to determine an uncertainty metric for the image, the controller is configured to:

convert the image, which uses a first color representation, to a second image that uses a different, second color representation;

perform a color detection to determine areas in the second image having the fluorescent color;

perform a pattern detection based on the color detection; and determine a likelihood that a detected pattern depicts damage to the part based on pattern matching with a defect model.

18. The part inspection system of claim 17, wherein to perform a pattern detection, the controller is configured to:

create a skeleton image based on the color detection; and perform a Hough transform of the skeletal image.

19. The part inspection system of claim 12, wherein the given frequency band includes ultraviolet light, and the part inspection system comprises a light filter situated between the part and a portion of either the camera or the lighting device when the camera records an image of the part, the light filter operable to prevent one or more of certain non-UV light and light polarizations from passing through the filter.

20. The part inspection system of claim 12, wherein the camera is part of a borescope, and is situated within the part when recording images of the part.

* * * * *